United States Patent [19]
Dou et al.

[11] Patent Number: 5,815,260
[45] Date of Patent: Sep. 29, 1998

[54] UROGENOUS COMPONENT MEASURING APPARATUS FOR QUALITATIVELY/ QUANTITATIVELY MEASURING A PLURALITY OF UROGENOUS COMPONENTS

[75] Inventors: Xiaoming Dou; Harumi Uenoyama; Yung Xiang Wang; Koji Matsuoka, all of Kyoto, Japan

[73] Assignee: Kyoto Dai-ichi Kagaku Co., Ltd., Minami-ku, Japan

[21] Appl. No.: 733,637

[22] Filed: Oct. 17, 1996

[30] Foreign Application Priority Data

Oct. 18, 1995 [JP] Japan .................................. 7-296227

[51] Int. Cl.⁶ .................................................. G01N 21/65
[52] U.S. Cl. .............................................................. 356/301
[58] Field of Search .............................................. 356/301

[56] References Cited

U.S. PATENT DOCUMENTS 5,553,616  9/1996  Ham et al. ........................ 250/339.07

FOREIGN PATENT DOCUMENTS 0 587 008  3/1994  European Pat. Off. .
0 637 742  2/1995  European Pat. Off. .

OTHER PUBLICATIONS

Goetz et al, "Application of a Multivariate Technique To Raman Spectra for Quantification of Body Chemicals", IEEE Transactions on Bio–Medical Electronics, vol. 42, No. 7, p. 728–731, Jul. 1995.

Gilmore et al, "Quantitative Detection of Environmentally Important Dyes Using Diode Laser/Fiber–Optic Raman Spectroscopy", Applied Spectroscopy, vol. 49, No. 4, p. 508–512, Apr. 1995.

Goetz et al, "Detection of Glucose Using Raman Spectroscopy", Proc. of the Annual Intern. Conf. of the IEEE Eng. in Medicine and Biology Soc., vol. 16, pp. 816–817, Nov. 3, 1994.

*Primary Examiner*—Vincent P. McGraw
*Attorney, Agent, or Firm*—Nikaido Marmelstein Murray & Oram LLP

[57] ABSTRACT

A concave urine collector is set under a front end portion of a stool body, so that urine can be collected in a bowl. Single fiber holes are set on a front end and a left side of the urine collector respectively, while condenser lenses for condensing light on the bowl side, an excitation light fiber member carrying excitation light from an excitation light source and a Raman light receiving fiber member for receiving Raman light are set in the fiber holes respectively. The excitation light fiber member is connected with the excitation light source, and the Raman light receiving fiber member communicates with a spectro-detector. A Raman signal separated into its spectral components detected by the spectro-detector is data-processed by a data processing part, and outputted from a data output part as a measurement result.

14 Claims, 17 Drawing Sheets

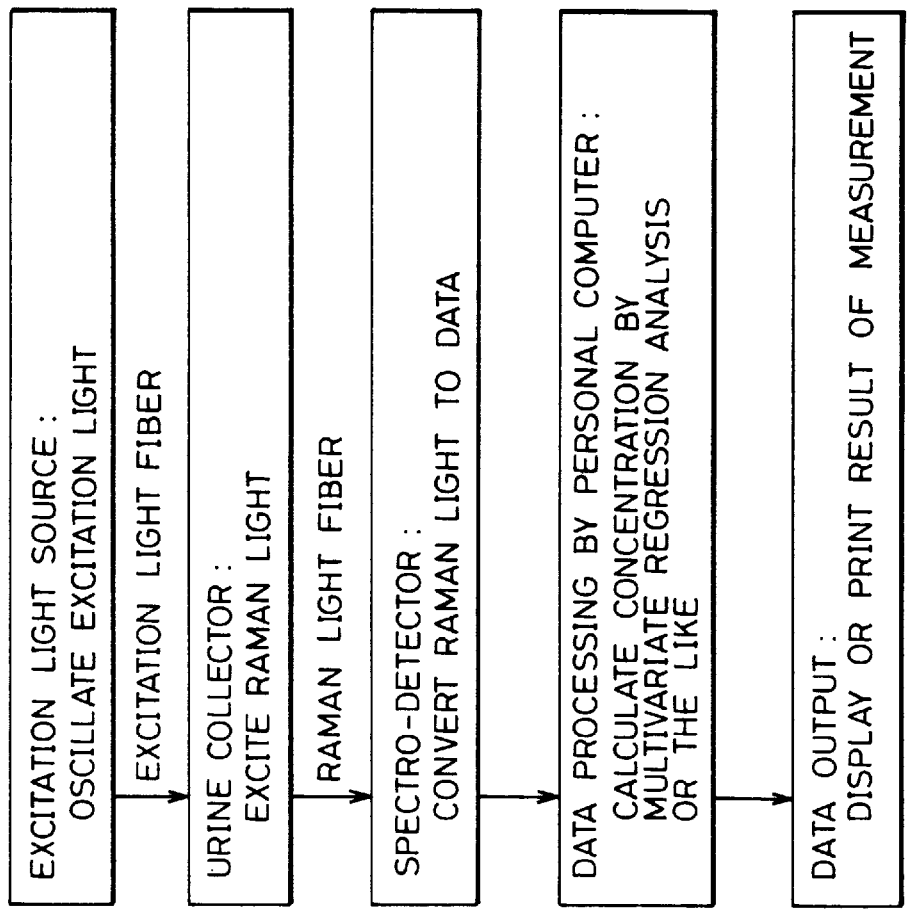
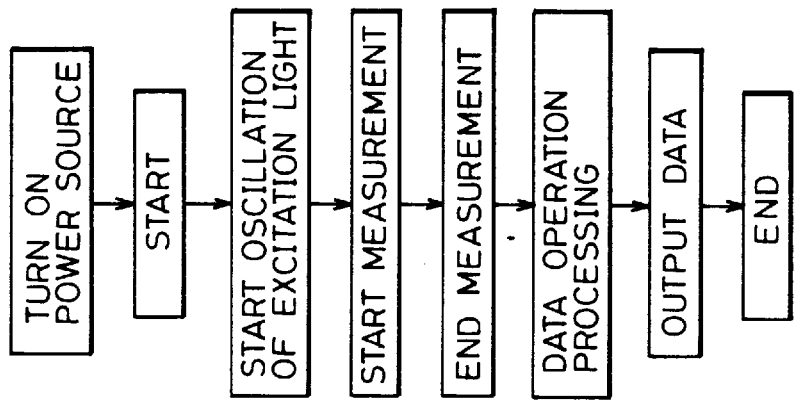

UROGENOUS COMPONENT MEASURING APPARATUS FOR QUALITATIVELY/ QUANTITATIVELY MEASURING A PLURALITY OF UROGENOUS COMPONENTS

BACKGROUND OF THE INVENTION

1. Field of the Invention

The present invention relates to a urogenous component measuring apparatus which is employed for urinalysis, and more particularly, it relates to a urogenous component measuring apparatus which is integrated with a stool, having a function of automatically collecting urine from the stool and qualitatively/quantitatively measuring a plurality of urogenous components at the same time.

2. Description of the Background Art

In consideration of easiness in collection of a urine specimen and a point that urine reflects fluctuation of a normal component existing in a body fluid or presence of an abnormal component in an early stage, urinalysis is employed not only for decision of various types of diseases but as an index for judgement of aftercare or therapy, to serve as means for grasping daily health.

While an individual can make urinalysis, this is not general since an experimental technique is necessary for the operation. A stool comprising a urinalysis test paper or a measurer has been developed as means for simplifying personal urinalysis. There have been proposed an apparatus for collecting part of urine in a prescribed portion of a stool and dipping a test paper therein for measuring urogenous glucose (refer to Japanese Patent Publication No. 5-39552 (1993)), an apparatus providing a urine collection chamber in a stool for measuring urogenous glucose or bilirubin with a reagent (refer to Japanese Patent Laying-Open Gazette No. 5-29266 (1993)), a method of adding a precipitant to urine collected from a stool for determining protein from the mass of the precipitate (refer to Japanese Patent Laying-Open Gazette No. 4-233457 (1992)), and an apparatus for collecting urine in a storer communicating with a stool and measuring sugar or uric acid (refer to Japanese Patent Publication No. 4-34445 (1992)).

However, it is common to the aforementioned apparatuses that expendables such as reagents and test papers are necessary for measuring urogenous components and measurement is made by an indirect method through intermediate reaction.

A decision method in the test paper method is mainly colorimetry, and a main reaction mechanism thereof is chemical reaction such as enzyme reaction or oxidation-reduction reaction. In the reagent method, colorimetry through an indicator or enzyme/chemical reaction or nephelometry employed for protein measurement is principal.

There also exists a biosensor employing an enzyme electrode.

However, every method has potential errors due to an indirect method through mediational reaction. Generally in the method making decision by colorimetry, errors are readily caused in decision of results, and the method through chemical reaction has low specificity. Further, a number of substances interfering with such examination are present in urine, and hence these interfering substances may inhibit reaction, cause false-positive reaction, or present a tone different from positive reaction to conceal the positive reaction. A system employing an enzyme is originally instable, and a system through chemical reaction is readily influenced by a coexistent substance. While the test paper method can measure a number of items at the same time, only semiquantitative analysis is possible.

The biosensor is also through enzyme reaction, resulting in a similar phenomenon. Further, although its technique is substantially established in measurement of glucose or uric acid, there are also substances which are still unmeasurable, and sensitivity and accuracy come into question.

In in-home examination by the test paper method, colorimetry is visually made, and hence its judgement varies with the individual and this cannot be regarded as strict examination.

In nosocomial examination, a patient himself must collect urine in a vessel such as a urine collection cup and hand it to a nurse or an examiner. In this case, the patient may feel ashamed.

SUMMARY OF THE INVENTION

An object of the present invention is to provide a urogenous component measuring apparatus for urinalysis which requires no expendables such as a reagent or a test paper, solves problems of preservation stability of an unused reagent and disposal of a biohazard substance, eliminates interference by a coexistent substance, can simultaneously determine various types of components contained in urine in a short time, requires no urine collection, can directly measure urine immediately after urination, and inflicts no mental pain on a patient.

In order to solve the aforementioned problems, an optical technique is employed in place of the reagent method or the test paper method generally employed as measuring means. Thus, no expendables such as a reagent or a test paper are necessary, whereby the problems of presevation stability of an unused reagent and disposal of a biohazard substance are solved, and a urogenous component measuring apparatus hardly subjected to interference by a coexistent substance due to no intermediate reaction such as enzyme reaction or chemical reaction with no concealment of a positive color by the tone of urine has been invented.

Further, measurement is made through Raman light which is specific to a target substance. Thus, a number of items can be simultaneously measured in a short time, while the patient may not feel ashamed since he or she urinates in a stool by ordinary means so that the urine is employed as a specimen for measurement.

Further, the apparatus can be manufactured without extremely changing the structure of a conventional stool.

According to the present invention, a specific Raman spectrum is obtained from each urogenous component in a target substance, for quantitatively measuring each component concentration from its spectral intensity and spectral pattern. The term "Raman" employed in the present invention includes not only Raman scattering in a narrow meaning but fluorescence, since fluorescence is also detected when fluorescence is generated.

As to each urogenous component to be measured, a shift wavenumber having a correlation coefficient R of at least 0.8, preferably at least 0.9, between the concentration and the specific Raman spectral intensity is selected as a measuring shift wavenumber which is specific to the component, a urine specimen is irradiated with Raman excitation light, a Raman spectral intensity at the measuring shift wavenumber selected for each of a plurality of urogenous components to be measured under the aforementioned condition is measured, and the plurality of urogenous components are simultaneously quantitatively analyzed by a previously formed calibration curve or multivariate regression analysis. The correlation coefficient R is provided as follows:

$$R = \frac{\sum_{i=1}^{n}(xi-X)(yi-Y)}{\sqrt{\left[\sum_{i=1}^{n}(xi-X)^2\right]\left[\sum_{i=1}^{n}(yi-Y)^2\right]}}$$

where xi represents the concentration of each point of each urogenous component, yi represents a Raman spectral intensity with respect to xi, X represents an average value of the concentration of each point of each urogenous component, and Y represents an average value of the Raman spectral intensity.

For example, FIG. 25 is a graph taking correlation coefficients R between the spectrum and the concentration on the axis of ordinates while taking shift wavenumber positions of 0 to 4000 cm$^{-1}$ of the spectrum on the axis of abscissas as to glucose. Through this graph, a shift wavenumber of at least 0.8, preferably at least 0.9, on the axis of ordinates may be selected as a measuring shift wavenumber.

If a urine specimen contains at least two components in the aforementioned components, however, respective component concentrations are calculated on the basis of spectral intensities with measuring shift wavenumbers which are set for the respective components in the aforementioned manner and at shift wavenumbers not overlapping with each other among Raman spectra obtained by irradiating the urine specimen with excitation light of a single wavelength and receiving scattered light from the urine specimen, in order to make determination without employing data processing such as multivariate regression analysis.

It is also possible to employ data processing such as multivariate regression analysis. The multivariate regression analysis operation is adapted to make data analysis through multivariate regression analysis such as principal component regression analysis (PCR) or a partial least square method (PLS method). In the multivariate regression analysis, regression analysis can be made by employing a number of spectral intensities at once, whereby quantitative analysis of higher accuracy as compared with single regression analysis is possible. While multiple regression analysis is most generally employed, a number of samples are required and its quantitative analysis accuracy is reduced if correlation between spectral intensities at respective shift wavenumbers is high. On the other hand, PCR which is multivariate regression analysis can intensify spectral intensities at a plurality of shift wavenumber regions to principal components which are irrelevant to each other and delete unnecessary noise data, whereby high quantitative analysis accuracy can be attained. Further, the PLS method can also utilize data of sample concentration in extraction of principal components, whereby high quantitative analysis accuracy can be attained similarly to the PCR. As to the multivariate regression analysis, "Tahenryo Kaiseki" (by Kazuo Nakatani, Shinyo-Sha) can be referred to.

In order to draw out necessary information from a spectrum complexly fluctuating by various fluctuation factors, data processing by a computer is remarkably useful. A typical processing method is stored in processing software provided in a commercially available near infrared apparatus or the like. As commercially available software, there is "Unscramber" by CAMO Company or the like. Typical processing methods are the aforementioned multiple regression analysis, PLS, the principal component regression analysis etc.

Large streams of data processing which is applied to quantitative regression analysis by multivariate regression analysis are (1) formation of a calibration model (calibration curve), (2) evaluation of the calibration model, and (3) determination of an unknown sample.

In order to perform calibration, it is necessary to measure a proper number of samples for forming a calibration curve in sufficient accuracy. Obtained spectra are subjected to preprocesses at need. Typical preprocesses are smoothing, differentiation and normalization of the spectra, which are general processes.

The calibration is processing of constructing mathematical relational expressions between spectral data and analytical values of target characteristics, i.e., models. Formation of models is performed by a statistical technique by employing analytical values of samples for forming a calibration curve and spectral data. In order to correctly evaluate accuracy of prediction of the prepared calibration curve with respect to an unknown sample, measurement errors with respect to the unknown sample are obtained through an evaluation sample. When the accuracy of the calibration curve is decided as being insufficient, the type of the processing method or parameters are changed at need, to correct the calibration curve.

A calibration curve which is recognized as having sufficient accuracy is employed as a relational expression for predicting values of target characteristics from spectral data in analysis of the unknown sample, to be used for determination of the unknown sample concentration.

FIG. 23 is a flow chart of a general procedure of multivariate regression analysis. Raman spectral measurement of a sample for preparing a calibration curve (having known analytical value) is performed, and preprocesses such as smoothing and normalization are performed at need, for thereafter forming a calibration model from obtained Raman spectral data (Raman spectral intensity at each wavenumber) by performing calibration through multivariate regression analysis.

Then, Raman spectral measurement of an evaluation sample (having known analytical value) for evaluating this calibration model is performed and preprocesses are performed at need, for thereafter substituting obtained Raman spectral data in the calibration model and comparing a measured value and a calculated value from the calibration model with each other, thereby evaluating accuracy of the calibration model. The process returns to the stages of the spectral measurement of the sample for preparing a calibration curve, preprocesses and formation of a calibration model, for correcting the calibration model and repeating evaluation by Raman spectral data of the evaluation sample if the accuracy is insufficient. If it is decided that sufficient accuracy is attained, on the other hand, Raman spectral data obtained by Raman spectral measurement of an unknown sample (having unknown analytical value) is substituted in this calibration model, for calculating the concentration.

As to the shift wavenumber employed for measurement, a shift wavenumber having a correlation coefficient of at least 0.8, preferably at least 0.9, between the concentration and the Raman spectral intensity can be selected as described above, while the shift wavenumber employed for measurement can alternatively be selected in an arbitrary wavelength range when multivariate regression analysis is employed.

The concentration of each urogenous component fluctuates with the urine volume. On the other hand, creatinine has a constant discharge volume per time. Therefore, it is preferable to contain creatinine as a urogenous component to be measured, for correcting other urogenous component concentrations with reference to a measured creatinine concentration. Thus, measured values correcting fluctuation of the urine volume can be obtained.

Urine passed by a user in a stool is collected in a concave urine collector in the stool. This urine is irradiated with Raman excitation light from an excitation laser, for example, to obtain Raman light. Obtained Raman spectral data are subjected to arithmetic processing, whereby a number of urogenous components can be qualitatively/quantitatively measured.

According to the inventive urogenous component measuring apparatus, urine collected in the urine collector is irradiated with Raman excitation light so that intensities at proper shift wavenumber positions or total spectral intensities are obtained as to a plurality of body fluid components to be measured from the obtained Raman light and a technique such as multivariate regression analysis is utilized, whereby a plurality of urogenous components can be simultaneously quantitatively analyzed in a short time, expendables such as a test paper or a reagent are unnecessary, and no problem of disposal after use arises. It is not necessary to collect urine, and an individual can readily make urinalysis. Further, influence by a coexistent substance is hardly exerted due to no enzyme reaction or chemical reaction, and measurement can be made with high accuracy.

In the inventive apparatus, a small hole for setting a scupper, an excitation light source, a Raman light receiving fiber member and a condensing fiber member may be provided in an existent stool while it is possible to cope with a spectral detection part, a data processing part and a data output part which are set in the exterior of the stool body by extremely simple ones, whereby no wide place is required. Therefore, it can be set in a space which is existent in a toilet of a house or a hospital. Further, the cost related to manufacturing/working may be reasonable since a relatively low-priced detector and the like are employed.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 7A is a flow chart showing the overall flow of an operation for making measurement by a urinalysis stool according to the present invention;

FIG. 7B is a flow chart showing operations of respective parts;

DESCRIPTION OF THE PREFERRED EMBODIMENTS

While some embodiments of the present invention are now described on the basis of the drawings, the present invention is not restricted by these.

Figure 1A:
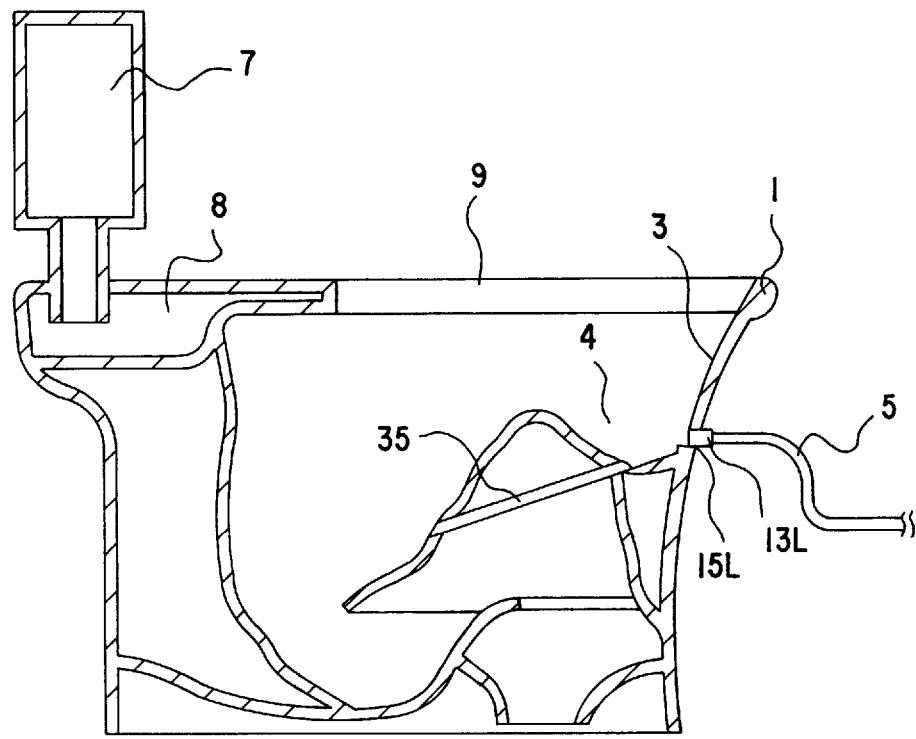
FIG. 1A is a side sectional view of a stool body according to an embodiment.
Figure 1B:
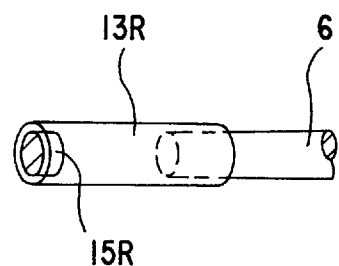
FIGS. 1B and 1C are perspective views showing an optical fiber member mounting part for the stool.
Figure 1C:
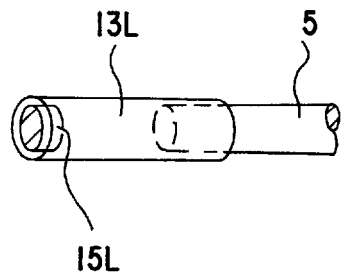

FIGS. 1A and 1B are a side sectional view and a plan sectional view of a stool body according to an embodiment of the present invention respectively. A stool hole 2 is formed in an upper surface of a stool body 1 to present a western-style stool shape similarly to the prior art, a water tank 7 storing wash water is set above a rear upper surface of the stool body 1 similarly to the prior art, and a water hole 9 is provided in an upper portion of the stool body 1. The wash water passes through a passage 8 from the water tank 7 and flows out from the water hole 9, to wash a bowl 3 and a urine collector 4.

The concave urine collector 4 is set under a front end portion of the stool body 1, so that urine can be collected in the bowl 3. Single fiber holes 13L and 13R are set on the front end and the left side of the urine collector 4 respectively, and condenser lenses 15L and 15R for condensing light are set on bowl 3 sides of these fiber holes 13L and 13R respectively, while an excitation light fiber member 5 for carrying excitation light from an excitation light source 14 (described later with reference to FIGS. 5 and 6) and a Raman light receiving fiber member 6 for receiving Raman light are set in the fiber holes 13L and 13R respectively.

FIG. 1B illustrates the inner parts of the fiber holes 13L and 13R in detail. The condenser lens 15L is set on the bowl 3 side of the fiber hole member 13L, in order to condense the excitation light outgoing from the excitation light fiber member 5 which is inserted in the stool body 1 outer side of the fiber hole 13L. On the other hand, the condenser lens 15R is set on the bowl 3 side of the fiber hole 13R for condensing the Raman light from a urine specimen in the urine collector 4, so that Raman light condensed here is received by the Raman light receiving fiber member 6 and guided to an optical system including a spectrodetector.

A scupper 35 is provided on the bottom portion of the urine collector 4, and the diameter of the scupper 35 is set at a size having such a passage resistance that the urine specimen remains in the urine collector 4 for at least a time necessary for measurement. While the urine flows from the urine collector 4 also during measurement, the urine does not disappear during the measurement. After the measurement, the urine remaining in the urine collector 4 continuously flows through the scupper 35 so that the urine collector 4 is vacated after a constant time. When the urine collector 4 is washed in a state storing the urine, the remaining urine is washed away with wash water, which in turn is collected in the urine collector 4. The wash water collected in the urine collector 4 also flows through the scupper 35, so that the urine collector 4 is vacated after a constant time.

Figure 2:
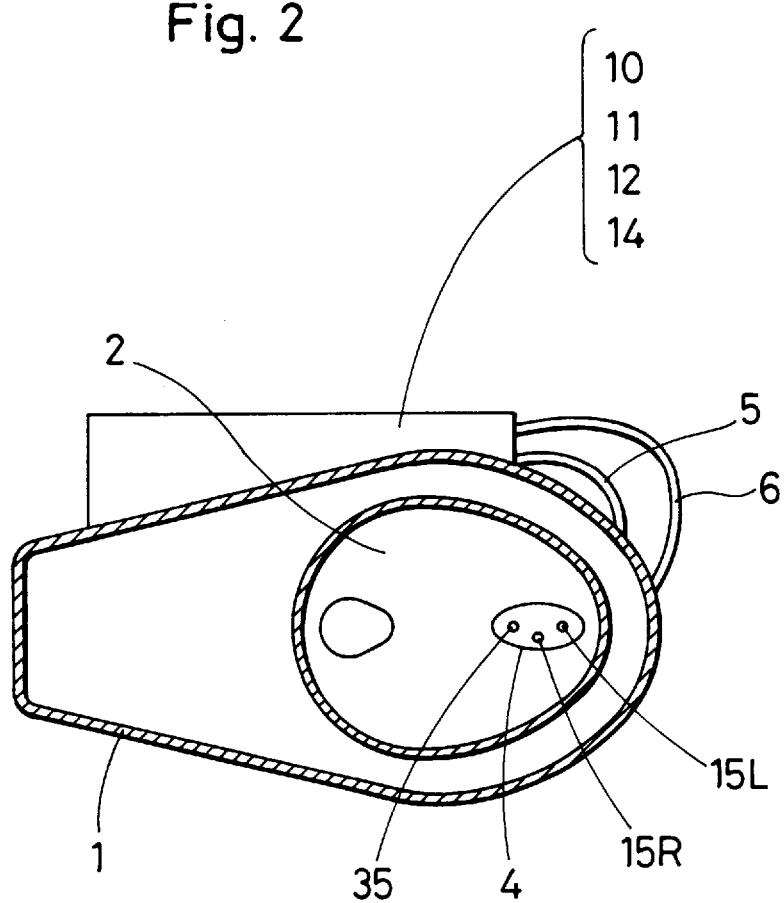
FIG. 2 is a plan sectional view of the stool body of the embodiment.

As shown in FIG. 2, the excitation light fiber member 5 is connected with the excitation light source 14 which is set in the exterior of the stool body 1, while the Raman light receiving fiber member 6 communicates with a spectrodetector 10 which is set in the exterior of the stool body 1. A Raman signal which is separated into its spectral components detected by the spectrodetector 10 is data-processed by a data processing part 11, and outputted from a data output part 12 as a measured value. Respective parts of the excitation light source 14, the spectrodetector 10, the data processing part 11 and the data output part 12 are described later with reference to FIGS. 5 and 6.

Figure 3:
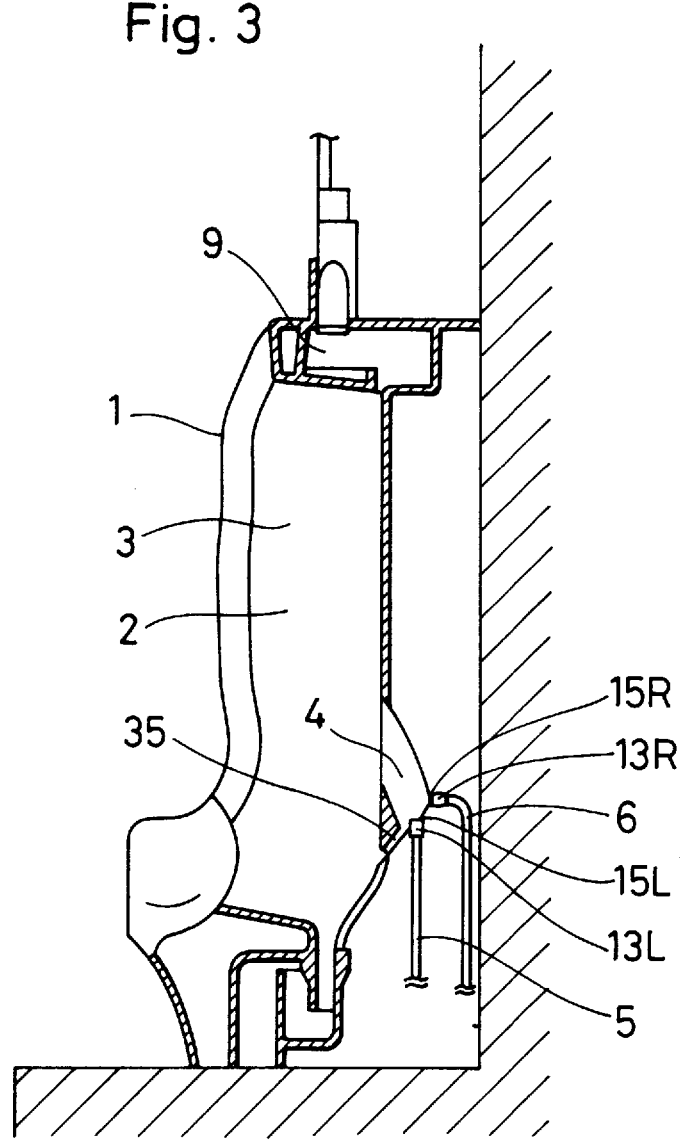
FIG. 3 is a side sectional view of a stool body according to another embodiment.
Figure 4:
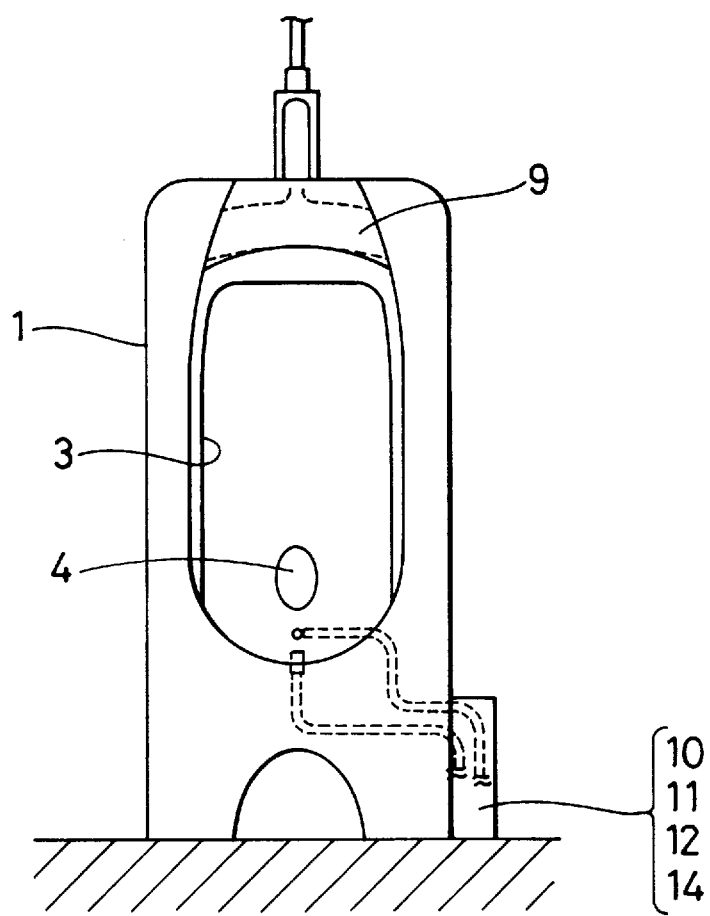
FIG. 4 is a front elevational view of the stool body according to the embodiment.

FIGS. 3 and 4 are a side elevational view and a front elevational view showing a stool body according to another embodiment of the present invention respectively.

Referring to FIG. 3, a stool hole 2 is formed on a front surface of the stool body 1 to present the shape of a urinal similarly to the prior art, and a water hole 9 is provided in an upper portion of the stool body 1, similarly to the prior art. Wash water flowing into a urine collector 4 from a bowl 3 flows through a scupper 35, to wash the urine collector 4.

According to this embodiment, the concave urine collector 4 is set in an inner lower portion of the stool body 1, so that urine can be collected in the bowl 3. Single fiber holes 13L and 13R are set on the lower end and the left side of the urine collector 4 respectively, and condenser lenses 15L and 15R for condensing light are set on bowl 3 sides of the fiber holes 13L and 13R respectively, while an excitation light fiber member 5 for carrying excitation light from an excitation light source 14 (described later with reference to FIGS. 5 and 6) and a Raman light receiving fiber member 6 for receiving Raman light are set in the fiber holes 13L and 13R respectively.

As shown in FIG. 4, the excitation light fiber member 5 is connected with the excitation light source 14 which is set in the exterior of the stool body 1, while the Raman light receiving fiber member 6 communicates with a spectrodetector 10 which is set in the exterior of the stool body 1, similarly to FIG. 2. A Raman signal which is separated into its spectral components detected by the spectrodetector 10 is data-processed by a data processing part 11, and outputted from a data output part 12 as a measured value.

Figure 5:
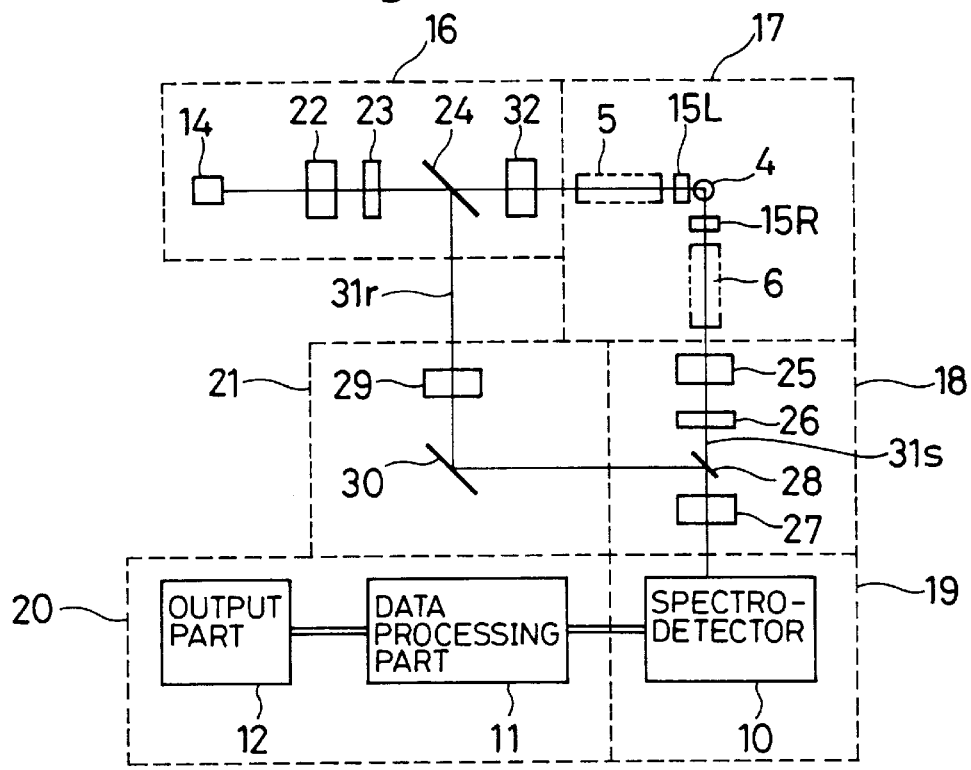
FIG. 5 is a block diagram mainly showing an optical system in an embodiment.

FIG. 5 is a block diagram showing mainly an optical system in an embodiment of the present invention, which consists of a light source part 16, a measuring/photoreceiving part 17, an optical target adjusting part 18, a spectro-detector part 19, a data processing and output part 20, and an optical correction adjusting part 21. The measuring/photoreceiving part 17 is set in a stool body 1, while the light source part 16, the optical target adjusting part 18, the spectro-detector part 19, the data processing and output part 20 and the optical correction adjusting part 21 are set in the exterior of the stool body 1.

Concretely describing, the light source part 16 comprises an excitation light source 14 generating single wavelength light, a bandpass filter 23 for transmitting only an excitation wavelength from the excitation light source 14 while reflecting the remaining light, a beam splitter 24 for dividing a beam from the excitation light source 14 into a sample beam 31s and a correction beam 31r, and a light source condenser lens 22 and a convergent lens 32 which are set on both sides of the beam splitter 24 for converging the sample beam 31s on a urine specimen in a urine collector 4 of the measuring/photoreceiving part 17. When the excitation light source 14 is a laser unit, it is preferable to provide a bandpass filter 23 for blocking off a sideband from its laser beam.

A laser unit, for example, is employed as the excitation light source 14. A continuously oscillating Kr ion laser, an He-Ne laser, a laser diode of InGaAs or the like, an Nd:YAG laser, or a pulse laser can be employed as the laser unit, and can be selected from lasers of a wide wavelength range over near ultraviolet to near infrared regions and utilized. As a light source other than the laser unit, a light source such as a halogen lamp generating multiwavelength light can be employed in combination with a spectroscope or an optical filter.

The wavelength of the excitation light is preferably at least 800 nm, i.e., in a longer wavelength region beyond near infrared. The reason for this is as follows: A vital component has large fluorescence, fluorescent luminous efficiency is high when excited with visible light of an Ar laser (514.5 nm) or an He-Ne laser (632.8 nm), and a spectrum is readily influenced by fluorescence, while the fluorescent luminous efficiency is reduced and influence of fluorescence can be reduced when excited with light of a longer wavelength region beyond near infrared and influence by external light of a fluorescent lamp forming stray light can be reduced.

An urine specimen is stored in a urine collector 4 and set in the measuring/photoreceiving part 17. The measuring/photoreceiving part 17 comprises an excitation light fiber member 5 for guiding the sample beam 31s, a condenser lens 15L for condensing the sample beam 31s from the excitation light fiber member 5 and irradiating the urine sample in the urine collector 4 with the sample beam 31s, the urine collector 4 for collecting the urine specimen and serving as a sample cell, a condenser lens 15R for converging Raman light generated from the urine specimen irradiated with the sample beam 31s, and a Raman light receiving fiber member 6 for receiving the Raman light obtained through the condenser lens 15R and guiding the Raman light to the spectrodetector part 19 through the optical target adjusting part 18.

The excitation light fiber member 5 and the Raman light receiving fiber member 6 may be single-core optical fiber members, or optical fiber bundles formed by bundling plural optical fiber members respectively.

The optical target adjusting part 18 comprises a filter 26 for removing the same wavelength component (Rayleigh light) as the excitation light from the obtained Raman light and taking out target light including fluorescence and Raman scattered light, and an optical system (condenser lenses 25 and 27) for adjusting beams.

The filter 26 is preferably either a holographic notch filter including the Rayleigh light light wavelength in its notch region, or a cut filter for blocking off the Rayleigh light wavelength and a shorter wavelength side. The holographic notch filter blocks only a desired wavelength region and transmits wavelength light of another region. It is possible to remove an excitation light component by employing that including the excitation light wavelength in the blocked region (notch region). The holographic notch filter is available on Kaiser Optical Systems, Inc. (U.S.A.), for example.

A beam splitter 28 is set between the filter 26 of the optical target adjusting part 18 and the condenser lens 27 as wave combining means, so that the target light is transmitted through the beam splitter 28 and guided to an inlet slit of a spectroscope of the spectro-detector 10 through the condenser lens 27.

The optical correction adjusting part 21 is adapted to guide the correction beam 31r divided by the beam splitter 24 to the beam splitter 28 of the wave combining means, and comprises a neutral density filter 29 for damping the light quantity and a reflecting mirror 30 for bending an optical path, in order to adjust the correction beam 31r. The correction beam 31r from the optical correction adjusting part 21 is reflected by the beam splitter 28, and guided to the inlet slit of the spectroscope of the spectro-detector 10 through the condenser lens 27.

The correction beam 31r includes only the excitation light from the excitation light source 14 and not through a sample, and hence the correction beam 31r does not depend on the sample but expresses intensity fluctuation from the light source in fidelity. The correction beam 31r is adapted to correct fluctuation of a spectral light intensity by fluctuation of the excitation light intensity from the excitation light source 14, and if such correction is unnecessary, the beam splitter 24 of the light source part 16, the optical correction adjusting part 21 and the beam splitter 28 which is wave combining means are unnecessary.

The spectro-detector part 19 comprises the single spectro-detector 10 comprising the spectroscope for incorporating a beam outgoing from the optical target adjusting part 18 and the correction beam 31r outgoing from the optical correction adjusting part 21 through the beam splitter 28 serving as wave combining means and separating the beam into spectral components thereof, and a detector for detecting the spectral components separated by the spectroscope.

The spectro-detector 10 is preferably a polychrometer comprising a multichannel photodetector for simultaneously detecting wavelength regions to be measured. When the spectro-detector 10 is a polychrometer, the wavelength regions to be measured can be simultaneously detected, and a target light spectrum of a prescribed region and the excitation light can be simultaneously detected. Consequently, no difference is caused between detection times for the respective wavelengths of the target light and the excitation light. If difference may be permitted between the detection times for the respective wavelengths of the target light and the excitation light, however, the spectro-detector part 19 may employ a wavelength scan type spectroscope or optical filters and a single channel photodetector for successively detecting the wavelength regions to be measured.

The data processing and output part 20 comprises a data processing part 11 for data-processing spectra detected by the detector of the spectro-detector 10, and an output part 12 for outputting data processed in the data processing part 11. The data processing part 11 is adapted to control operations of the respective parts as well as perform data processing such as multivariate regression analysis on a signal detected by the spectro-detector 10 while including a function of correcting a detected intensity of the target light with reference to a detected intensity of the excitation light component in the spectra detected by the spectro-detector 10, forms a Raman scattering spectrum in which fluctuation of the light source is corrected, and performs qualification and determination of the sample from the target light intensity. The output part 12 is a printer or a display outputting the data processed in the data processing part 11.

While it is assumed that $\theta=90°$ in this embodiment assuming that $\theta$ represents an angle formed by scattered light from a target substance with respect to incident light, the present invention is not restricted to this so far as $0° \leq \theta < 360°$.

Figure 6:
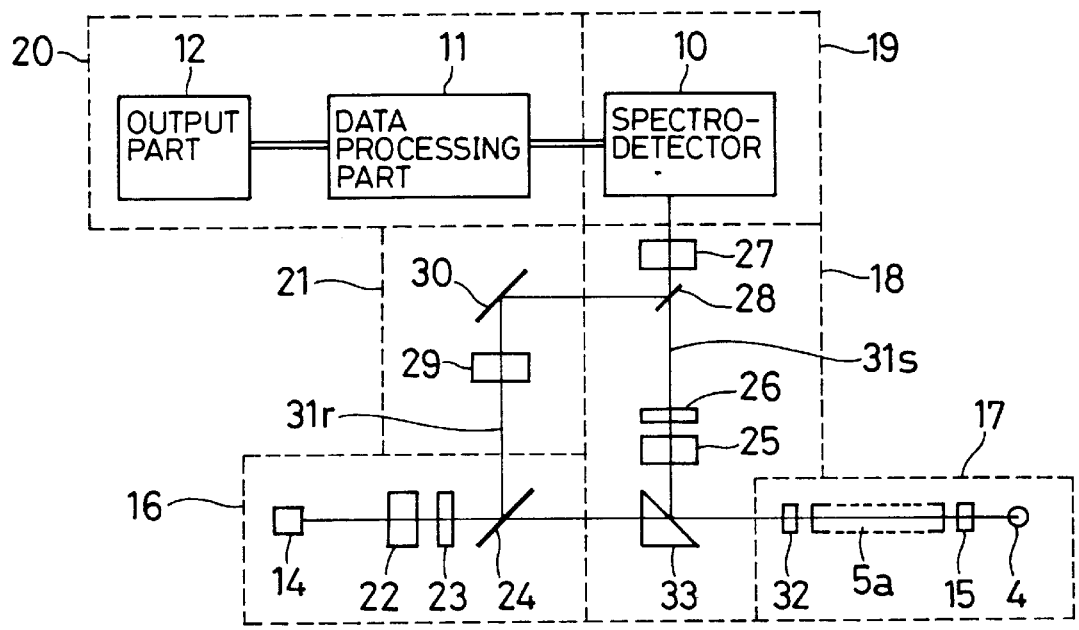
FIG. 6 is a block diagram mainly showing an optical system in another embodiment.

FIG. 6 shows an apparatus in case of $\theta=180°$, and parts common to those of the apparatus shown in FIG. 5 are denoted by the same reference numerals.

A sample beam 31s from an excitation light source part 16 is transmitted through a central transmitting reflecting mirror 33 which has a central hole and is arranged in an optical target adjusting part 18, to be applied to a urine specimen in a measuring/photoreceiving part 17 through an optical fiber member 5a. The optical target adjusting part 18 is similar to that shown in FIG. 5, and provided with condenser lenses 25 and 27 for converging Raman light from the urine specimen passing through the optical fiber member 5a and reflected by the mirror 33 in an inlet slit of a spectroscope of a spectro-detector 10, while a holographic notch filter which is set to include a wavelength of excitation light in its notch region is arranged between the condenser lenses 25 and 27 as a filter 26 for removing the same wavelength component as the excitation light and taking out target light. The remaining structure other than the measuring/photoreceiving part 17 is identical to that of FIG. 5.

In the embodiment of FIG. 6, the optical fiber member 5a serves both as an excitation light fiber member and a Raman light receiving fiber member. Also in this case, the optical fiber member 5a may be a single-core optical fiber member, or an optical fiber bundle formed by bundling a plurality of optical fiber members. In case of an optical fiber bundle, it is possible to distinguishedly use the same for using a part as an excitation light fiber member and the remaining part as a Raman light receiving fiber member.

In the optical systems of FIGS. 5 and 6, transparent plate glass members such as slide glass can be employed as the beam splitters 24, 28 and 33. When transparent plate glass members are obliquely arranged on optical paths, it is possible to separate single incident light into reflected light and transmitted light, and combine transmitted incident light and reflected incident light on the same optical axis. Half mirrors may be employed in place of the transparent plate members. When transparent plate glass members are employed, the transmitted light quantity can be increased since there is no absorption as to transmitted light, dissimilarly to the half mirrors.

FIGS. 7A and 7B are flow charts showing the overall flow of an operation for measuring the urine specimen in the urine collector 4 by the urinalysis stool according to the present invention and showing operations of the respective parts respectively.

When a power source provided in the exterior of the stool body 1 is turned on, the apparatus operation is started from a measurement preparation state. Oscillation of the excitation light and measurement are started. Raman light of the urine specimen in the urine collector 4 excited by the excitation light source 14 is received by the Raman light receiving fiber member 6, and the measurement is ended after Raman spectrum measurement of a prescribed time. Results obtained by processing the obtained Raman spectral data by performing proper data analysis operation are outputted as concentrations of respective components etc. The power source is automatically turned off after completion of data output.

The data processing part 11 analyzes the measured data by mathematical arithmetic processing such as multivariate regression analysis on the basis of intensities of Raman light separated into its spectral components by the spectrodetector 10 or spectral patterns and obtains respective component concentrations. The analytical results are outputted to the data output part 12.

The data processing part 11 can also perform operation of correcting concentrations of other components with reference to a creatinine concentration.

In order to start the measurement, the scupper 35 in FIG. 1A may be formed by a transparent glass tube so that the measurement is automatically started when the urine specimen passes through the scupper 35, in place of a method of manually pushing a start button.

Results of measurement on some components contained in urine are shown. Data shown in FIGS. 8 to 22 are results of measurement as to aqueous solution samples of respective single components.

Figure 8:
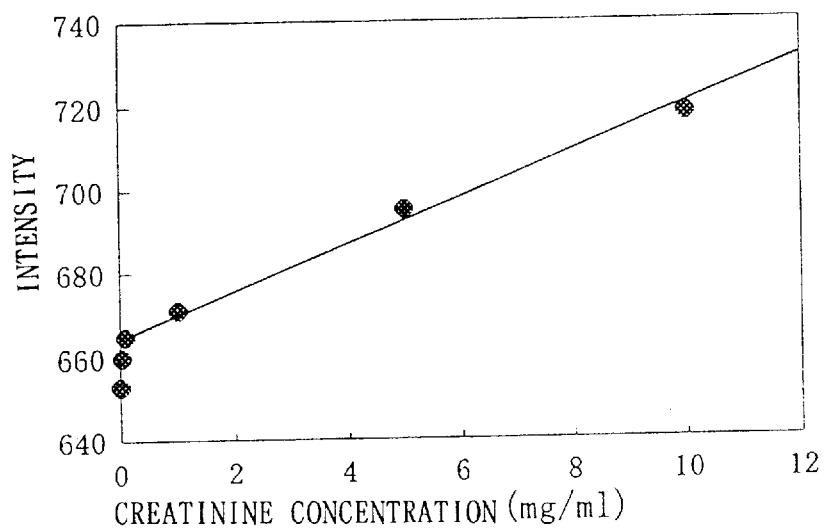
FIG. 8 illustrates the correlation between creatinine concentrations and Raman scattered light intensities.

FIG. 8 shows a result of investigation of correlation between spectral intensities and concentrations of creatinine, and a multiple correlation coefficient $R^2$ (square of correlation coefficient R) is 0.961.

Figure 9:
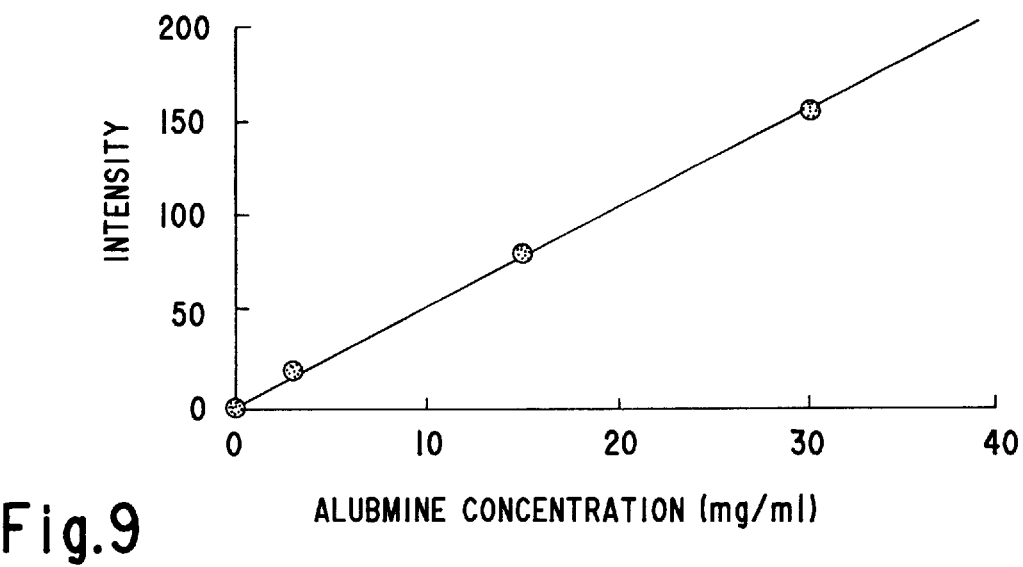
FIG. 9 illustrates the correlation between albumin concentrations and Raman scattered light intensities.
Figure 10:
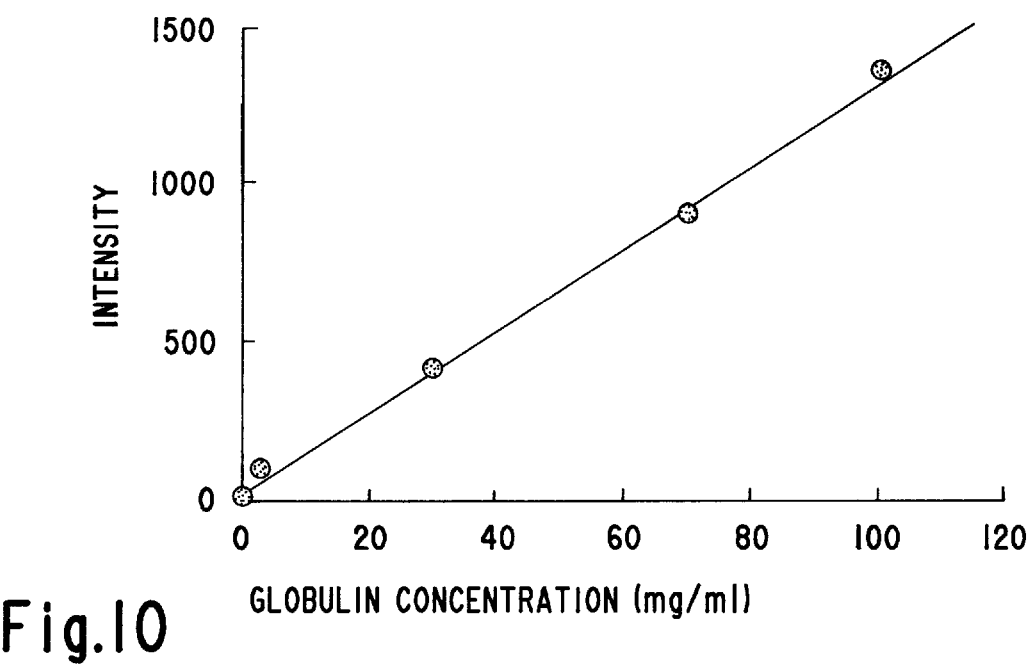
FIG. 10 illustrates the correlation between globulin concentrations and Raman scattered light intensities.
Figure 11:
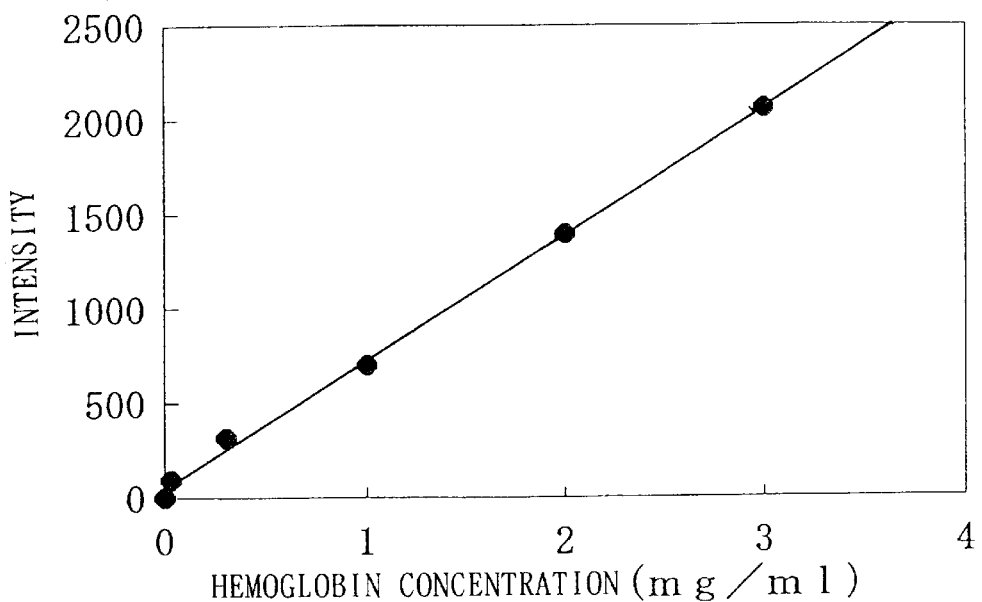
FIG. 11 illustrates the correlation between hemoglobin concentrations and Raman scattered light intensities.

FIGS. 9 to 11 show results of determination as to protein in urine. Albumin and globulin serve as indices for nephrosis syndrome or glomerulonephritis, and hemoglobin serves as an index for inflammation or tumor of the urinary system or the like.

FIG. 9 shows the result of investigation of correlation between spectral intensities and concentrations of albumin, and the multiple correlation coefficient $R^2$ is 0.999.

FIG. 10 shows the result of investigation of correlation between spectral intensities and concentrations of globulin, and the multiple correlation coefficient $R^2$ is 0.994.

FIG. 11 shows the result of investigation of correlation between spectral intensities and concentrations of hemoglobin, and the multiple correlation coefficient $R^2$ is 0.998.

FIGS. 12 to 15 show results of determination as to sugar in urine. Glucose, lactose, fructose and galactose serve as indices for diabetes mellitus, infantile dyspepsia, alimentary levulosemia and critical hepatopathy or infantile trophopathy respectively.

Figure 12:
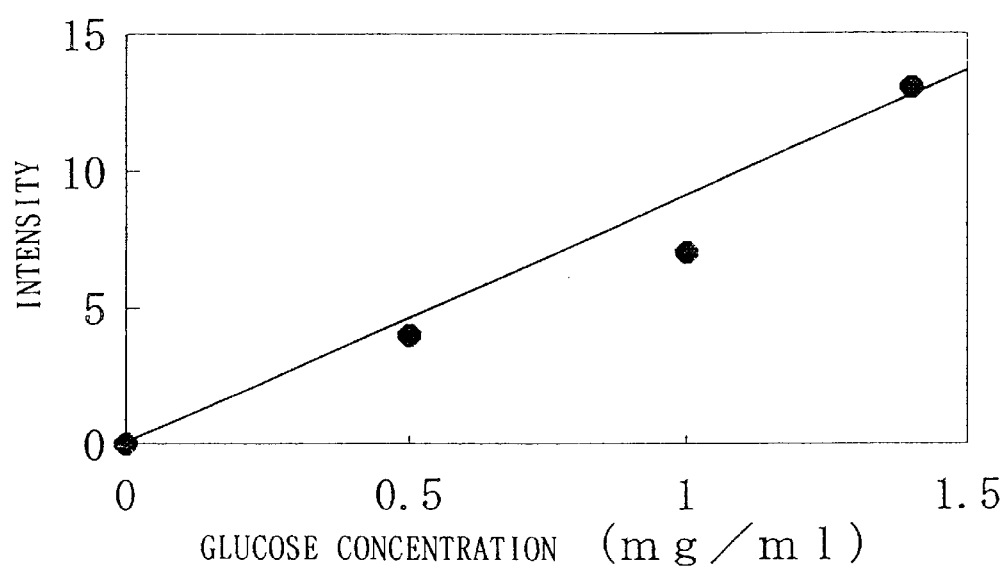
FIG. 12 illustrates the correlation between glucose concentrations and Raman scattered light intensities.

FIG. 12 shows the result of investigation of correlation between spectral intensities and concentrations of glucose, and the multiple correlation coefficient $R^2$ is 0.964.

Figure 13:
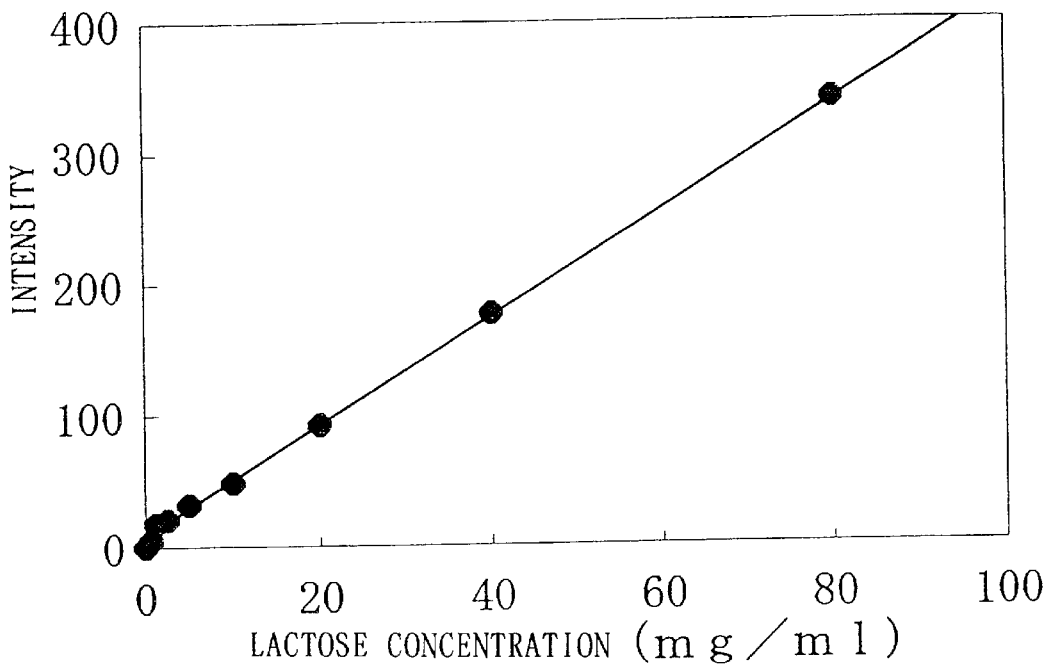
FIG. 13 illustrates the correlation between lactose concentrations and Raman scattered light intensities.

FIG. 13 shows the result of investigation of correlation between spectral intensities and concentrations of lactose, and the multiple correlation coefficient $R^2$ is 0.999.

Figure 14:
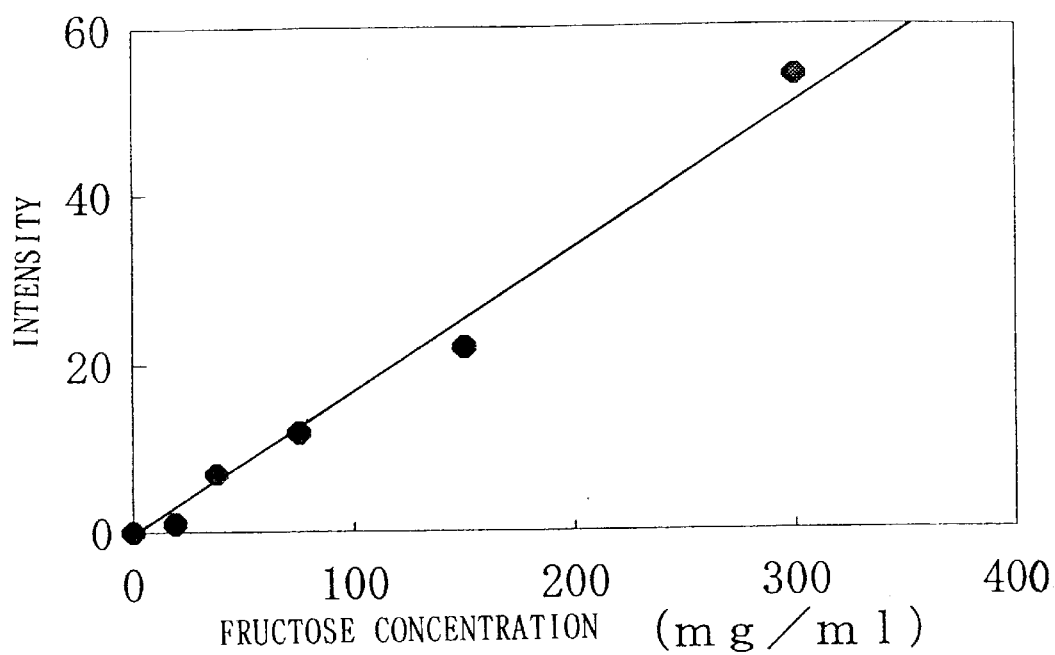
FIG. 14 illustrates the correlation between fructose concentrations and Raman scattered light intensities.

FIG. 14 shows the result of investigation of correlation between spectral intensities and concentrations of fructose, and the multiple correlation coefficient $R^2$ is 0.990.

Figure 15:
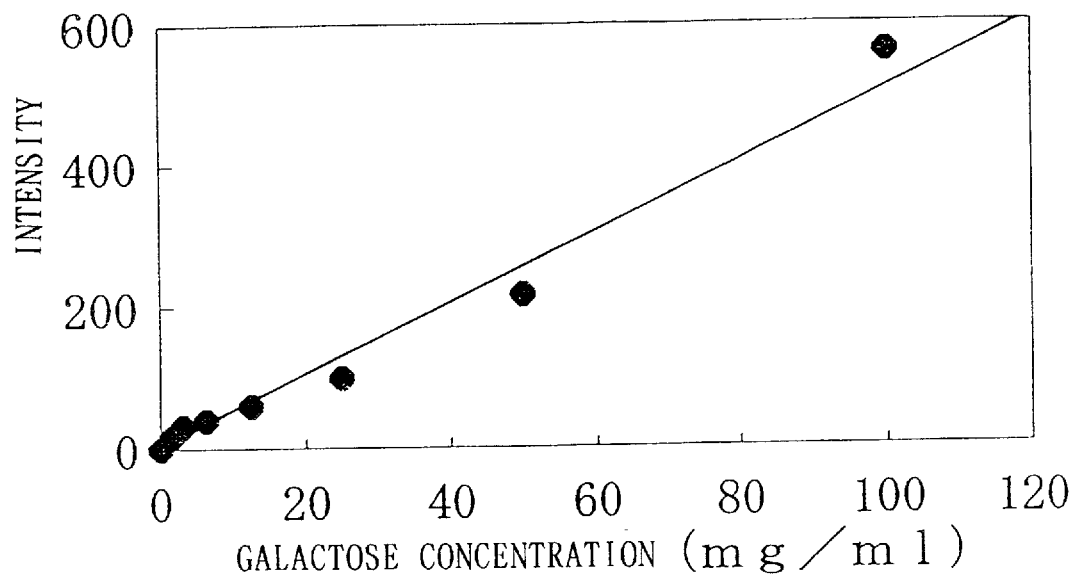
FIG. 15 illustrates the correlation between galactose concentrations and Raman scattered light intensities.

FIG. 15 shows the result of investigation of correlation between spectral intensities and concentrations of galactose, and the multiple correlation coefficient $R^2$ is 0.974.

Figure 16:
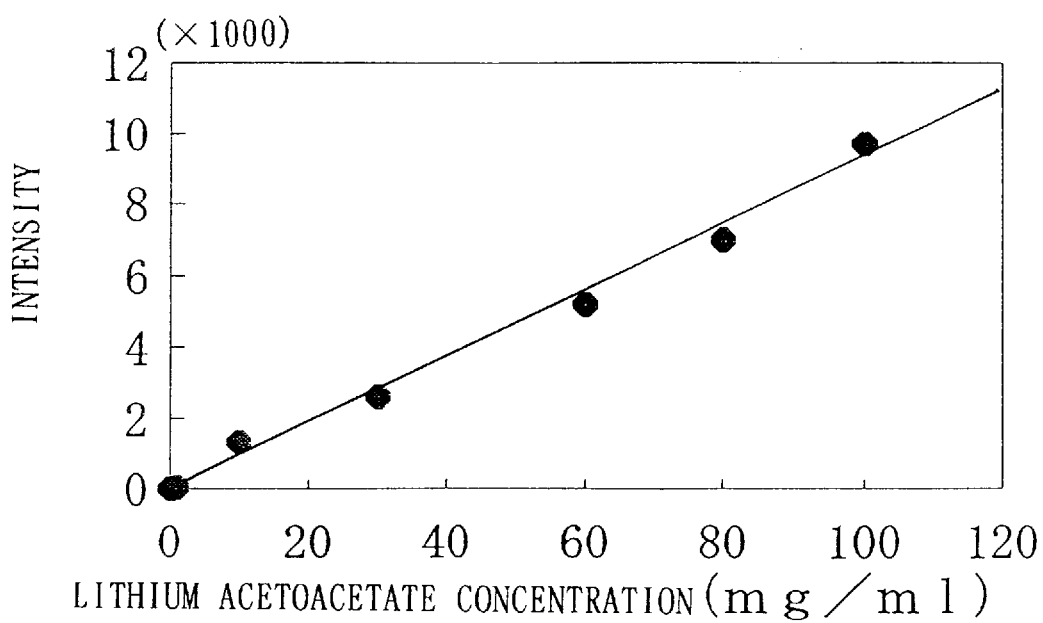
FIG. 16 illustrates the correlation between lithium acetoacetate concentrations and Raman scattered light intensities.
Figure 17:
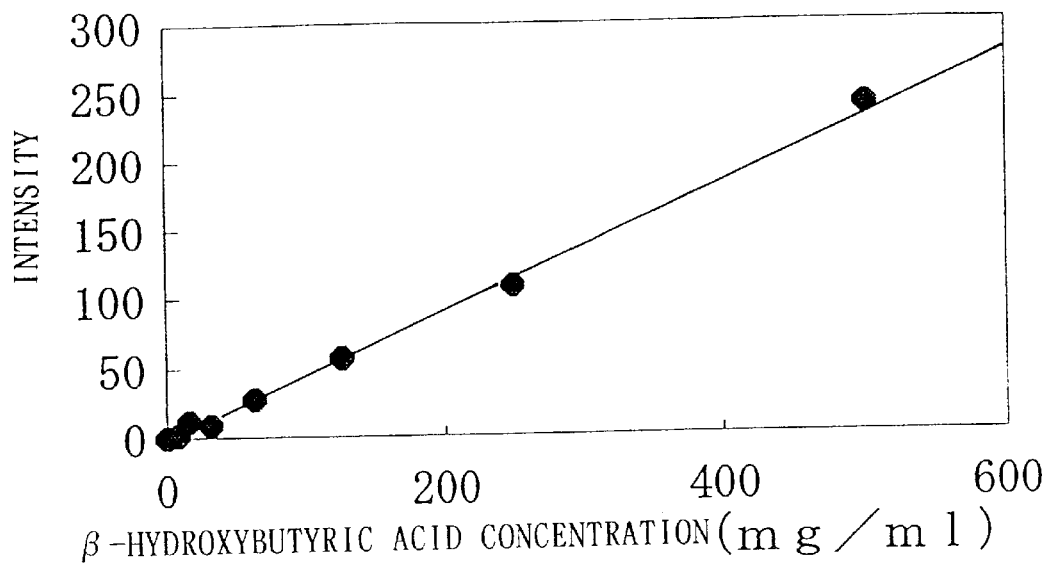
FIG. 17 illustrates the correlation between β-hydroxybutyric acid concentrations and Raman scattered light intensities.
Figure 18:
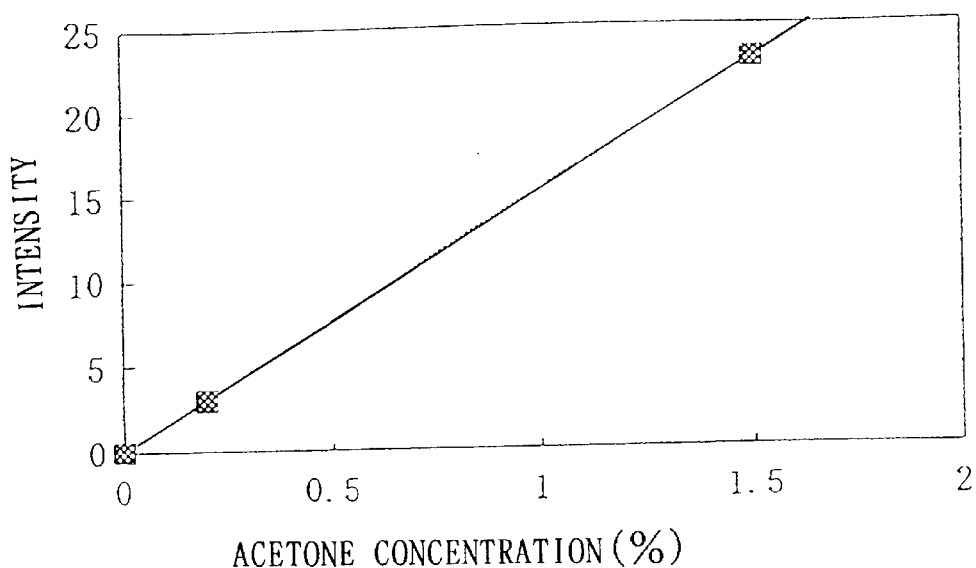
FIG. 18 illustrates the correlation between acetone concentrations and Raman scattered light intensities.

FIGS. 16 to 18 show results of determination as to ketone bodies in urine. Lithium acetoacetate, β-hydroxybutyric acid and acetone serve as indices for ketoacidosis or the like.

FIG. 16 shows the result of investigation of correlation between spectral intensities and concentrations of lithium acetoacetate, and the multiple correlation coefficient $R^2$ is 0.998.

FIG. 17 shows the result of investigation of correlation between spectral intensities and concentrations of β-hydroxybutyric acid, and the multiple correlation coefficient $R^2$ is 0.997.

FIG. 18 shows the result of investigation of correlation between spectral intensities and concentrations of acetone, and the multiple correlation coefficient $R^2$ is 0.999.

Figure 19:
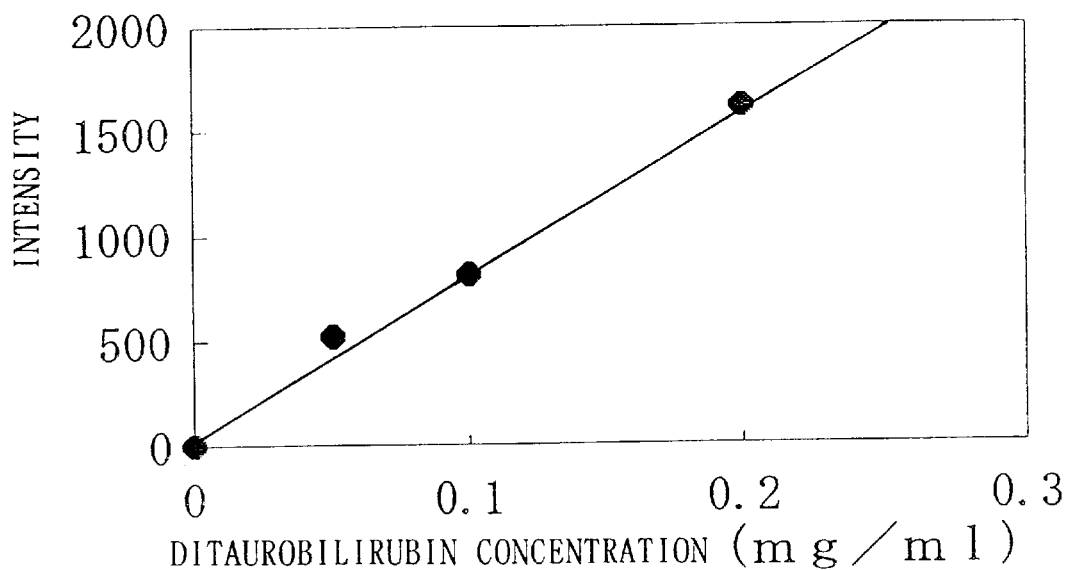
FIG. 19 illustrates the correlation between ditaurobilirubin concentrations and Raman scattered light intensities.
Figure 20:
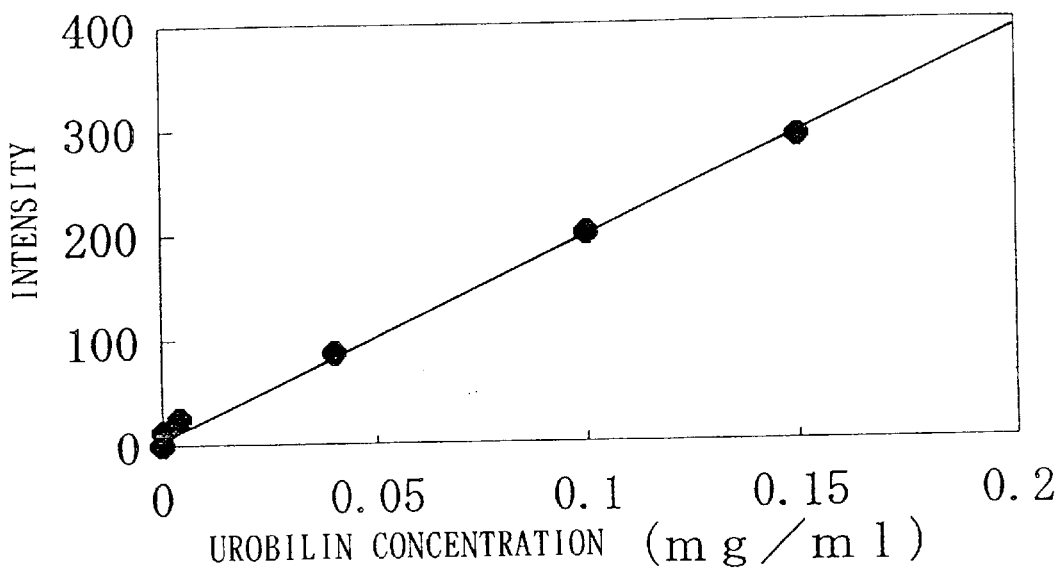
FIG. 20 illustrates the correlation between urobilin concentrations and Raman scattered light intensities.

FIGS. 19 and 20 show results of determination as to bile pigments in urine. Bilirubin and urobilinogen serve as indices for hepatic/biliary disease and hepatic/biliary disease or cythemolytic disease respectively. Since bilirubin is insoluble in water, ditaurobilirubin was employed in this example. As to urobilin, measurement was made with urobilin since urobilinogen is instable and readily becomes urobilin by air oxidation.

FIG. 19 shows the result of investigation of correlation between spectral intensities and concentrations of ditaurobilirubin, and the multiple correlation coefficient $R^2$ is 0.994.

FIG. 20 shows the result of investigation of correlation between spectral intensities and concentrations of urobilin, and the multiple correlation coefficient $R^2$ is 0.995.

Figure 21:
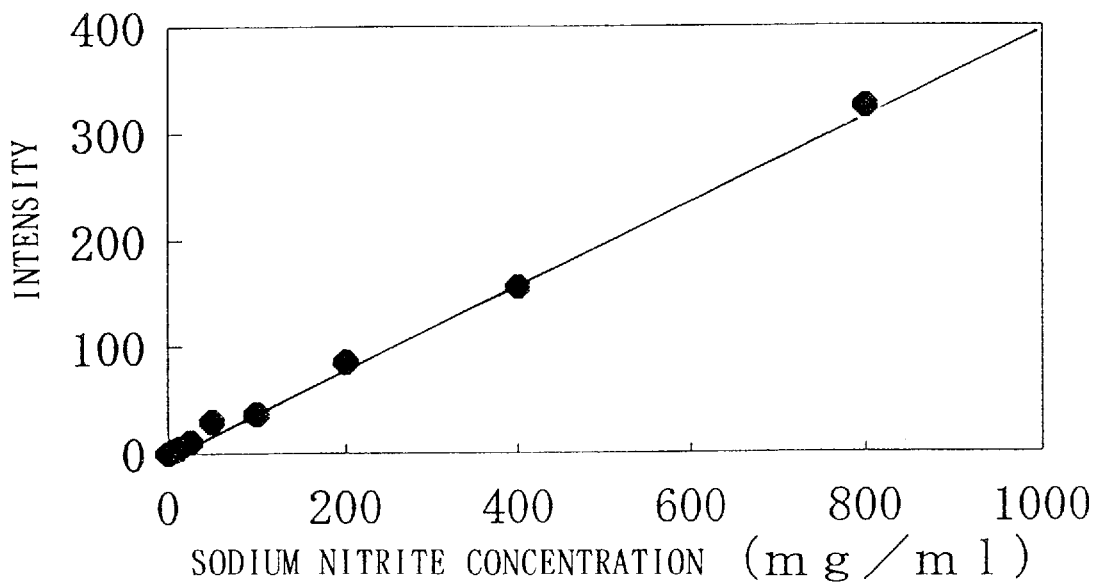
FIG. 21 illustrates the correlation between sodium nitrite concentrations and Raman scattered light intensities.

FIG. 21 shows the result of determination as to nitrite in urine, and the multiple correlation coefficient $R^2$ of its spectral intensities and concentrations is 0.998.

Sodium nitrite serves as an index for microbism of a urinary system.

Figure 22:
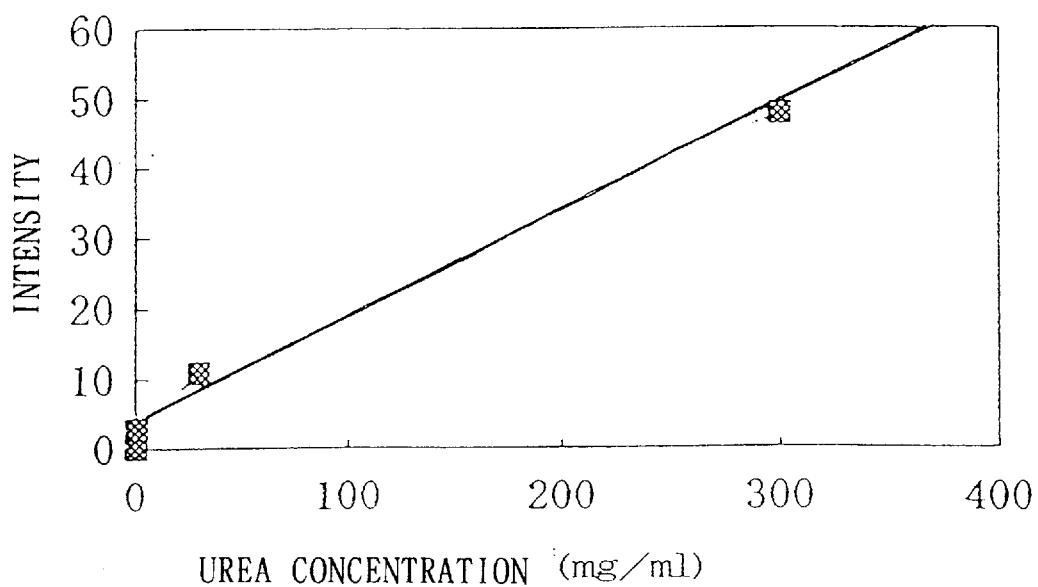
FIG. 22 illustrates the correlation between urea concentrations and Raman scattered light intensities.

FIG. 22 shows the result of determination as to urea in urine, and the multiple correlation coefficient $R^2$ of its spectral intensities and concentrations is 0.998. Urogenous urea is useful for recognizing internal protein metabolism, liver/renal function or the like. Sthenia of body protein catabolism or dosage of quinine is conceivable if it is increased, while hepatocytic affection or renal insufficiency is conceivable if it is reduced. It has also been recognized that the urogenous urea volume serves as an index of urine specific gravity ("Shintei Rinsho Kensa Kenshu Handbook 3" by Nozomu Kosakai, Yakujinippo-Sha), while osmotic pressure* refractive index and urine specific gravity are generally excellent in relation, and determination of the three is substituted by specific gravity ("Rinsho Kensaho Teiyo" by Masamitsu Kanai, Kinbara Shuppan Kabushiki Kaisha).

Figure 23:
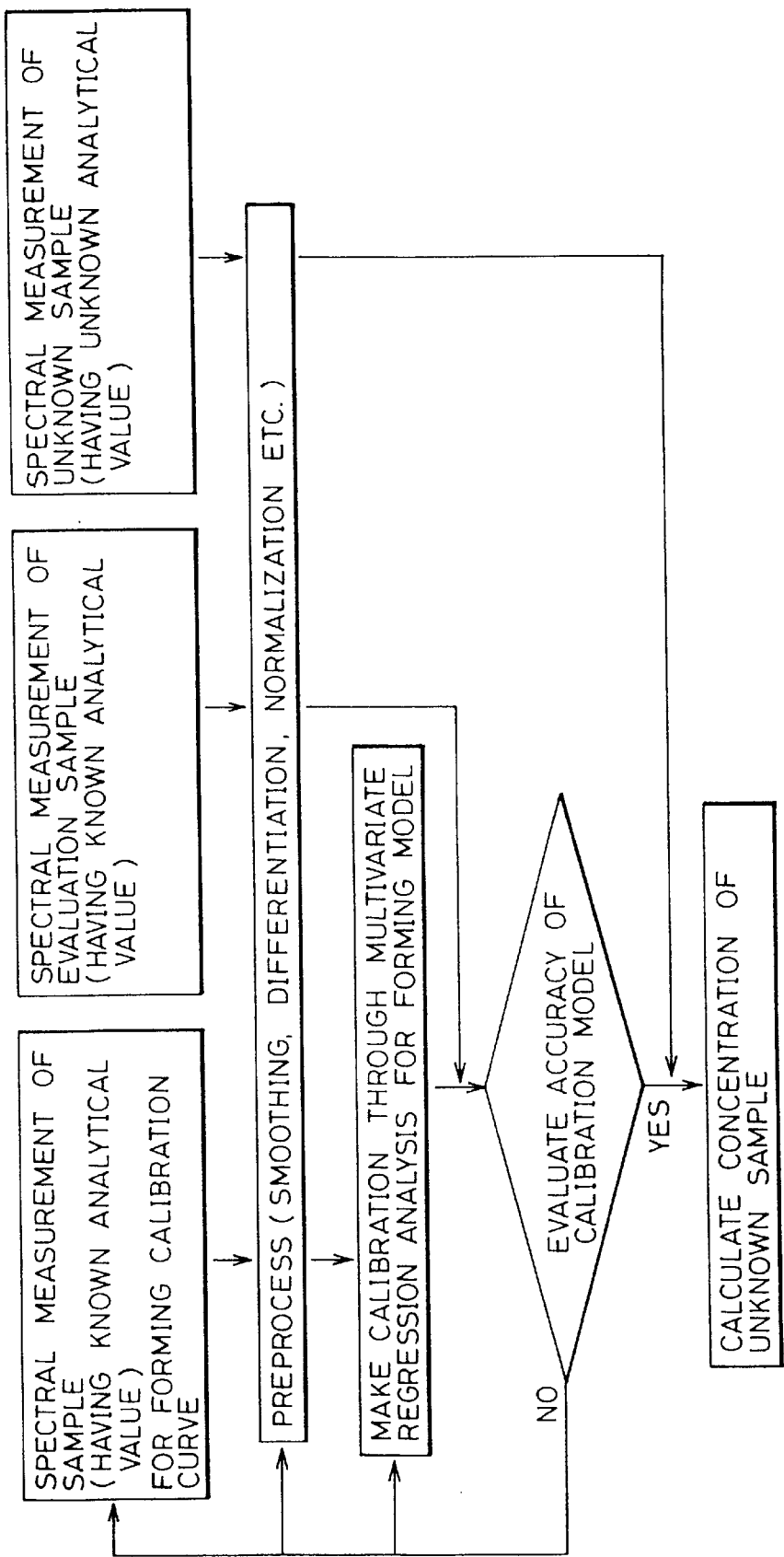
FIG. 23 is a flow chart showing a procedure from spectral measurement to concentration determination by multivariate regression analysis.
Figure 24A:
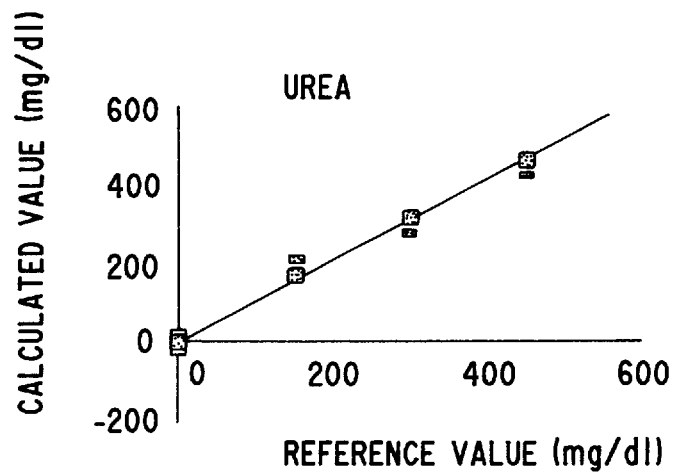
FIG. 24 shows correlation diagrams of calculated values and actual values of a plurality of urogenous components calculated by multivariate regression analysis.
Figure 24B:
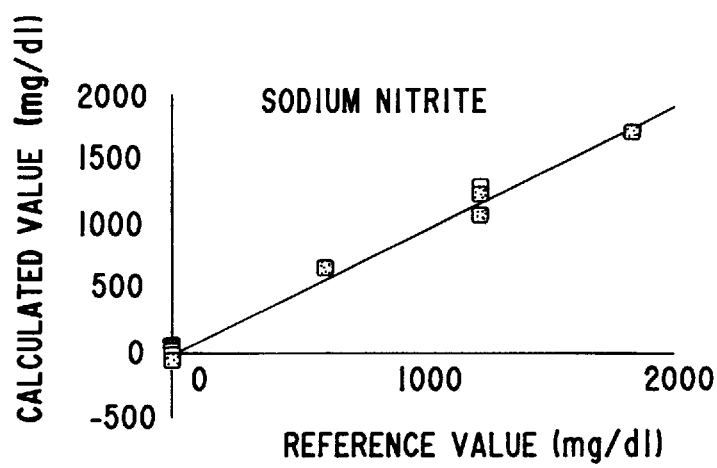
Figure 24C:
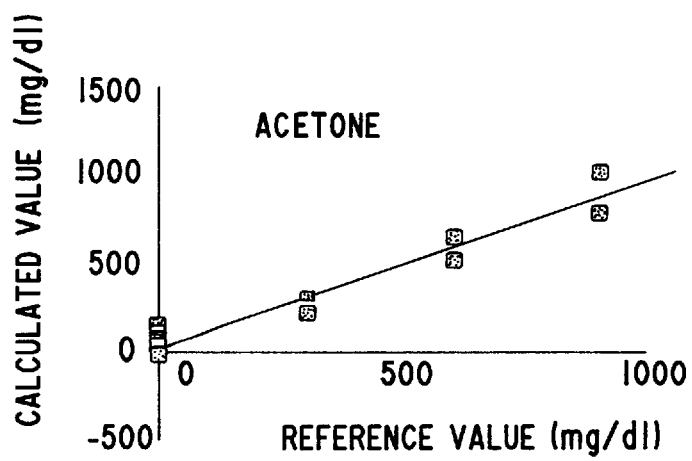
Figure 25:
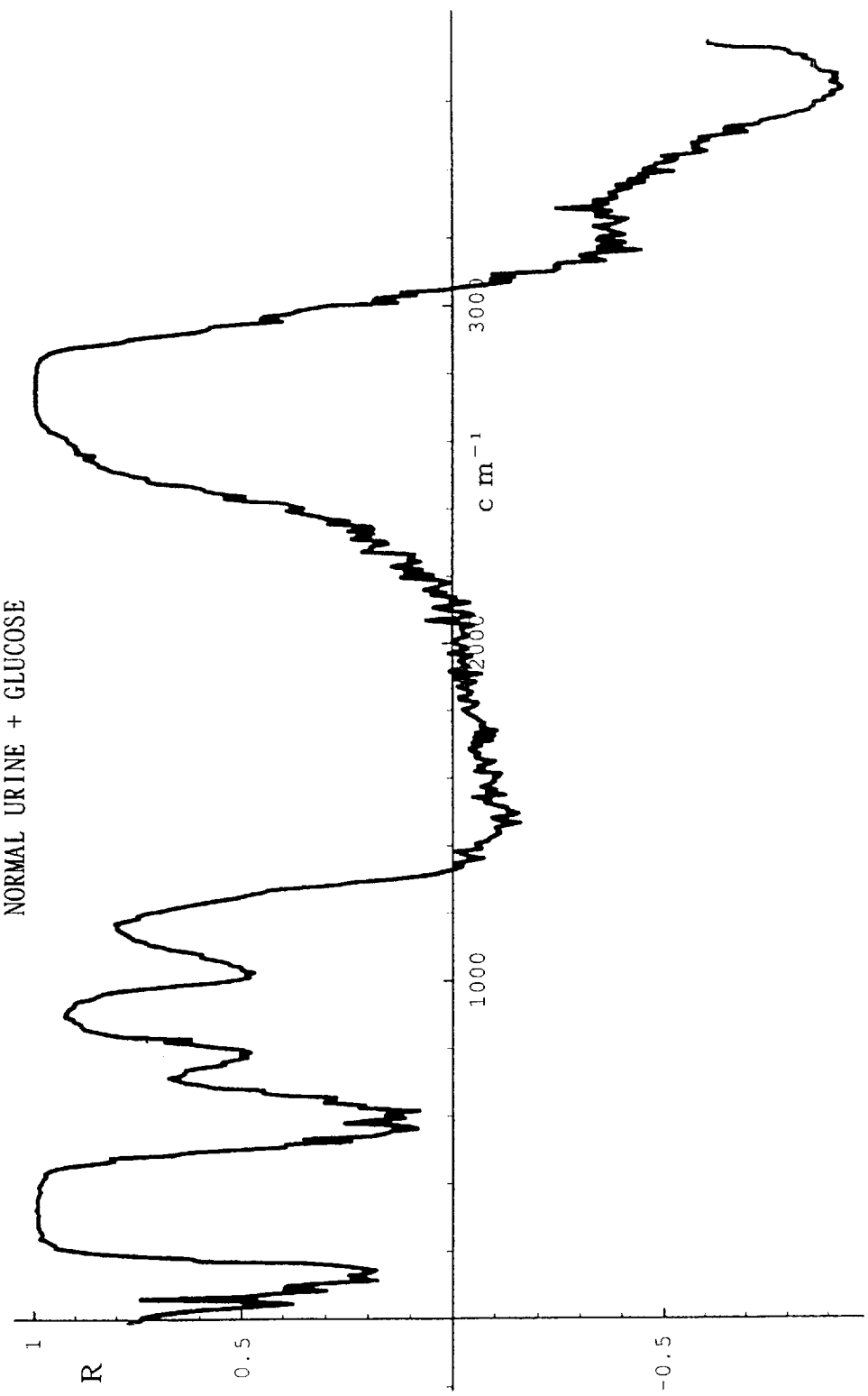
FIG. 25 is a graph taking correlation coefficients between the spectrum and the concentration on the axis of ordinates while taking shift wavenumber of 0 to 4000 $cm^{-1}$ of the spectrum on the axis of abscissas as to glucose.

FIGS. 23 and 24 illustrate examples employing multivariate regression analysis.

150 mg/dl, 300 mg/dl and 450 mg/dl of urea, 600 mg/dl, 1.2 g/dl and 1.8 g/dl of sodium nitrite and 300 mg/dl, 600 mg/dl and 900 mg/dl of acetone were added to normal urine in arbitrary combinations respectively, spectra were measured, and concentrations were determined by multivariate regression analysis.

The concentration of an arbitrary substance existing in urine can be approximated by the following equation:

$$C = \sum_{i=1}^{n} k(\lambda i) \cdot A(\lambda i)$$

where C represents the concentration of the arbitrary substance existing in urine, $k(\lambda i)$ represents a proportional constant at a shift wavenumber i $cm^{-1}$, and $A(\lambda i)$ represents a Raman spectral intensity at the shift wavenumber i $cm^{-1}$.

The value $k(\lambda i)$ is decided in the procedure of multivariate regression analysis, so that the correlation between the concentration of a sample having a known analytical value and an estimated concentration is maximized. This calculation is previously integrated into commercially available processing software and automatically performed, so that this equation is formed every urogenous substance whose concentration is to be obtained.

FIG. 23 is a flow chart showing the procedure from spectral measurement to concentration determination. In this example, no pretreatment was performed and QUANT+ by Perkin Elmer Co., Ltd. was employed as processing software. The PCR method was employed as the processing method. When full cross validation is performed, evaluation of accuracy of a calibration model can be omitted.

FIG. 24 shows correlation diagrams of calculated values and actual values (reference values) obtained in this example. Multiple correlation coefficients $R^2$ and SEP of urea, sodium nitrite and acetone were 0.986 and 18.13, 0.992 and 57.17, and 0.956 and 69.74 respectively. SEP indicates a predicted standard error, which is calculated as follows:

$$SEP = \sum_{i=1}^{n} (di - D)^2/(n-1)^2$$

where di represents the difference between a calculated value by a calibration model and an actual value, D represents an average value of di, and n represents the number of evaluation samples.

As this numerical value is reduced, it indicates that accuracy of the calibration curve is high.

Although the present invention has been described and illustrated in detail, it is clearly understood that the same is by way of illustration and example only and is not to be taken by way of limitation, the spirit and scope of the present invention being limited only by the terms of the appended claims.

We claim:

1. A urogenous component measuring apparatus comprising:
    a stool body;
    a urine collector being provided in said stool body on a position for receiving urine;
    an excitation light source part for generating excitation light of a visible or infrared wavelength region;
    a measuring/photoreceiving part for irradiating a urine specimen in said urine collector with said excitation light from said excitation light source part and receiving target light including Raman light generated from said urine specimen being irradiated with said excitation light;
    an optical system including a spectro-detector for incorporating said target light being received in said measuring/photoreceiving part and measuring either a Raman spectral intensity at a selected measuring shift wavenumber or a Raman spectral intensity at each shift wavenumber in an arbitrary shift wavenumber range as to a urogenous component to be measured;
    a data processing part for incorporating said Raman spectral intensity measured value obtained in said optical system for calculating at least one urogenous component concentrations on the basis thereof; and
    a data output part for outputting a data analysis result by said data processing part.

2. The urogenous component measuring apparatus in accordance with claim 1, wherein
    said measuring shift wavenumber being selected for said urogenous component to be measured is a shift wavenumber being specific to said component having excellent correlation between a concentration and a Raman spectral intensity in aqueous solution measurement of said urogenous component, and
    said data processing part holds calibration curve data indicating relations between concentrations and Raman spectral intensities at respective measuring shift wavenumbers as to a plurality of urogenous components, for incorporating Raman spectral intensity measured values at said respective measuring shift wavenumbers as to said plurality of urogenous components and simultaneously qualitatively/quantitatively analyzing said plurality of urogenous components through said calibration curve data.

3. The urogenous component measuring apparatus in accordance with claim 2, wherein
    said measuring shift wavenumber is a shift wavenumber having a correlation coefficient R of at least 0.8 in aqueous solution measurement of said urogenous component.

4. The urogenous component measuring apparatus in accordance with claim 1, wherein
    said measuring shift number being selected as to said urogenous component to be measured is a shift wavenumber being specific to said component having excellent correlation between a concentration and a Raman spectral intensity in aqueous solution measurement of said urogenous component, and
    said data processing part incorporates Raman spectral intensity measured values at respective measuring shift wavenumbers as to a plurality of urogenous components and simultaneously qualitatively/quantitatively analyzes said plurality of urogenous components by multivariate regression analysis.

5. The urogenous component measuring apparatus in accordance with claim 4, wherein
    said measuring shift wavenumber is a shift wavenumber having a correlation coefficient R of at least 0.8 in aqueous solution measurement of said urogenous component.

6. The urogenous component measuring apparatus in accordance with claim 1, wherein
    said data processing part incorporates Raman spectral intensity measured values at respective wavelengths in an arbitrary wavelength range as to a plurality of urogenous components and simultaneously qualitatively/quantitatively analyzes said plurality of urogenous components by multivariate regression analysis.

7. The urogenous component measuring apparatus in accordance with claim 1, containing creatinine as said urogenous component to be measured, wherein said data processing part corrects other urogenous component concentrations with reference to a creatinine concentration.

8. The urogenous component measuring apparatus in accordance with claim 1, wherein
    said spectro-detector comprises a multichannel photodetector for simultaneously detecting Raman spectral intensities at a plurality of shift wavenumbers.

9. The urogenous component measuring apparatus in accordance with claim 1, wherein a scupper is provided on a base portion of said urine collector, and the diameter of said scupper is set at a size having such a passage resistance that said urine specimen remains in said urine collector for at least a time required for measurement.

10. The urogenous component measuring apparatus in accordance with claim 1, wherein said excitation light source part generates said excitation light including light of at least 800 nm in wavelength.

11. The urogenous component measuring apparatus in accordance with claim 10, wherein said excitation light source of said excitation light source part is a semiconductor laser.

12. The urogenous component measuring apparatus in accordance with claim 1, wherein said excitation light source part and said optical system including said spectro-detector are set in the exterior of said stool body, and an optical fiber member is provided between said urine collector and said excitation light source part and said optical system as a light transmission path.

13. The urogenous component measuring apparatus in accordance with claim 3, wherein the shift wavenumber has a correlation coefficient R of at least 0.9.

14. The urogenous component measuring apparatus in accordance with claim 5, wherein the shift wavenumber has a correlation coefficient R of at least 0.9.

\* \* \* \* \*